United States Patent [19]

Hayashi et al.

[11] Patent Number: 5,902,899

[45] Date of Patent: May 11, 1999

[54] PROCESS FOR PREPARING 1, 3-DISUBSTITUTED UREA

[75] Inventors: Taketo Hayashi; Junichi Yasuoka, both of Osaka, Japan

[73] Assignee: Sumika Fine Chemicals Co., Ltd., Osaka, Japan

[21] Appl. No.: 08/985,363

[22] Filed: Dec. 4, 1997

[30] Foreign Application Priority Data

Dec. 5, 1996 [JP] Japan .................................. 8-342575
Jan. 8, 1997 [JP] Japan .................................. 9-013438

[51] Int. Cl.$^6$ ........................ C07C 273/18; C07C 275/06
[52] U.S. Cl. .......................... 564/58; 546/306; 549/480; 564/32; 564/47; 564/48; 564/55; 564/57; 564/61
[58] Field of Search .................. 564/47, 48, 55, 564/57, 61, 63, 32, 58; 549/229, 230

[56] References Cited

FOREIGN PATENT DOCUMENTS

| 1176976 | 2/1982 | Canada . |
| 0066922 | 12/1982 | European Pat. Off. . |
| 60-163853 | 8/1985 | Japan . |
| 62-009107 | 2/1987 | Japan . |
| 62-017572 | 4/1987 | Japan . |

OTHER PUBLICATIONS

V. Papesch et al., J. Org. Chem., 16, 1879–1890 (1951).
J. Izdebski et al., Synthesis, 6, 423–425 (1989).

*Primary Examiner*—Shailendra Kumar
*Attorney, Agent, or Firm*—Birch, Stewart, Kolasch & Birch, LLP

[57] ABSTRACT

Process for preparing 1,3-disubstituted urea of the formula:

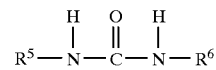

wherein $R^5$ is the same as or different from $R^6$, and each of $R^5$ and $R^6$ is independently linear or branched, alkyl of 1–20 carbon atoms, alkenyl group having 2 to 20 carbon atoms or alkynyl group having 2 to 20 carbon atoms, which may have phenoxy, alkoxy of 1–13 carbon atoms, monocycloalkyl of 3–8 carbon atoms, bicycloalkyl of 6–12 carbon atoms, aryl of 6–13 carbon atoms, furyl, pyridyl, or aralkyl of 7–20 carbon atoms, comprising reacting cyclic carbonic acid ester with an amine using alkali metal alkoxide or trialkylamine as base, in safety and high yield.

3 Claims, No Drawings

PROCESS FOR PREPARING 1,3-DISUBSTITUTED UREA

BACKGROUND OF THE INVENTION

1. Field of the Invention

The present invention related to a process for preparing a 1,3-disubstituted urea, and more particularly to a process for preparing a 1,3-disubstituted urea which is useful as an intermediate for the preparation of pharmaceuticals and agricultural chemicals.

2. Discussion of Related Art

Conventionally, as methods for preparing a 1,3-disubstituted urea, there have been proposed, for instance, (1) a method for preparing a 1,3-disubstituted urea comprising reacting a primary amine with phosgene as disclosed in J. Org. Chem., 16 (1951) p.1879–1890, (2) a method for preparing a 1,3-disubstituted urea comprising reacting a primary amine with isocyanate as disclosed in J. Org. Chem., 16 (1951) p.1879–1890, (3) a method for preparing a 1,3-disubstituted urea comprising reacting a primary amine or a secondary amine with carbon monoxide as disclosed in Japanese Unexamined Patent Publication No. 60-163853, (4) a method for preparing a 1,3-disubstituted urea comprising reacting a primary amine with carbon dioxide as disclosed in Japanese Examined Patent Publication No. 62-9107, (5) a method for preparing a 1,3-disubstituted urea comprising reacting a primary amine with a cyclic carbonic acid ester as disclosed in Japanese Examined Patent Publication No. 62-17572, (6) a method for preparing a 1,3-disubstituted urea comprising reacting a primary amine or a secondary amine with bis(4-nitrophenyl) carbonate as disclosed in Synthesis, 6 (1989) p.423–425, and the like.

However, the above methods (1) and (2) have defects in workability and safety because those methods necessitate toxic phosgene and isocyanate as starting materials.

The above methods (3) to (5) have defects in the yield of a 1,3-disubstituted urea. In order to increase the yield, the above methods necessitate severe reaction conditions such as high temperatures and high pressures or an excess amount of a primary amine. When the severe reaction conditions are employed, a large and complex apparatus is necessitated. Also, when the excess amount of the primary amine is used, there is a defect in the separation and recovery of the unreacted primary amine after the reaction.

Also, the above method (6) has a defect in economics because the method necessitates expensive bis(4-nitrophenyl)carbonate as a starting material.

An object of the present invention is to provide a process for preparing a 1,3-disubstituted urea, excellent in workability, safety, yield and economics.

These and other objects of the present invention will be apparent from the following descriptions.

SUMMARY OF THE INVENTION

In accordance with the present invention, there are provided (1) a process for preparing a symmetric 1,3-disubstituted urea, represented by the formula (III):

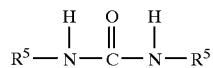

(III)

wherein $R^5$ is a linear or branched, alkyl group having 1 to 20 carbon atoms, alkenyl group having 2 to 20 carbon atoms or alkynyl group having 2 to 20 carbon atoms, which may have phenoxy group or an alkoxy group having 1 to 13 carbon atoms, a monocycloalkyl group having 3 to 8 carbon atoms, a bicycloalkyl group having 6 to 12 carbon atoms, an aryl group having 6 to 13 carbon atoms, furyl group, pyridyl group, or an aralkyl group having 7 to 20 carbon atoms, comprising reacting a cyclic carbonic acid ester represented by the formula (I):

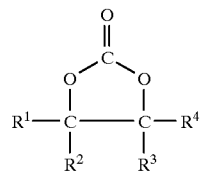

(I)

wherein each of $R^1$, $R^2$, $R^3$ and $R^4$ is independently hydrogen atom or a linear or branched alkyl group having 1 to 5 carbon atoms, and $R^1$ or $R^2$ may form a ring together with $R^3$ or $R^4$, with an amine represented by the formula (II):

$R^5$—$NH_2$ (II)

wherein $R^5$ is the same as defined above, in the presence of an alkali metal alkoxide having 1 to 12 carbon atoms or a trialkylamine having 3 to 12 carbon atoms as a base; and (2) a process for preparing an unsymmetric 1,3-disubstituted urea represented by the formula (V):

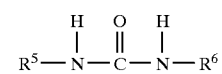

(V)

wherein $R^5$ is a linear or branched, alkyl group having 1 to 20 carbon atoms, alkenyl group having 2 to 20 carbon atoms or alkynyl group having 2 to 20 carbon atoms, which may have phenoxy group or an alkoxy group having 1 to 13 carbon atoms, a monocycloalkyl group having 3 to 8 carbon atoms, a bicycloalkyl group having 6 to 12 carbon atoms, an aryl group having 6 to 13 carbon atoms, furyl group, pyridyl group, an aralkyl group having 7 to 20 carbon atoms or allyl group; and $R^6$ is different from $R^5$ and is a linear or branched, alkyl group having 1 to 20 carbon atoms, alkenyl group having 2 to 20 carbon atoms or alkynyl group having 2 to 20 carbon atoms, which may have phenoxy group or an alkoxy group having 1 to 13 carbon atoms, a monocycloalkyl group having 3 to 8 carbon atoms, a bicycloalkyl group having 6 to 12 carbon atoms, an aryl group having 6 to 13 carbon atoms, furyl group, pyridyl group, or an aralkyl group having 7 to 20 carbon atoms, comprising reacting a cyclic carbonic acid ester represented by the formula (I):

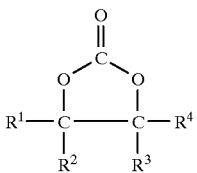
(I)

wherein each of $R^1$, $R^2$, $R^3$ and $R^4$ is independently hydrogen atom or a linear or branched alkyl group having 1 to 5 carbon atoms, and $R^1$ or $R^2$ may form a ring together with $R^3$ or $R^4$, with an amine represented by the formula (II):

(II)

wherein $R^5$ is the same as defined above, in the absence of a base at a temperature of 0° to 180° C.; and thereafter with an amine represented by the formula (IV):

(IV)

wherein $R^5$ is the same as defined above, in the presence of an alkali metal alkoxide having 1 to 12 carbon atoms or a trialkylamine having 3 to 12 carbon atoms as a base.

DETAILED DESCRIPTION OF THE INVENTION

In the process for preparing a 1,3-disubstituted urea of the present invention, a cyclic carbonic acid ester represented by the formula (I):

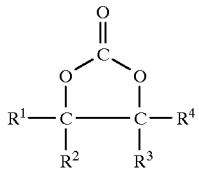
(I)

wherein each of $R^1$, $R^2$, $R^3$ and $R^4$ is independently hydrogen atom or a linear or branched alkyl group having 1 to 5 carbon atoms, and $R^1$ or $R^2$ may form a ring together with $R^3$ or $R^4$, is used as a starting material.

The 1,3-disubstituted urea is obtained by reacting the cyclic carbonic acid ester with a specific amine.

The 1,3-disubstituted urea is classified into a symmetric 1,3-disubstituted urea and an unsymmetric 1,3-disubstituted urea. The cyclic carbonic acid ester used in the preparation of the symmetric 1,3-disubstituted urea as a starting material is the same as that used in the preparation of the unsymmetric 1,3-disubstituted urea as a starting material. However, a process for preparing the symmetric 1,3-disubstituted urea is different from a process for preparing the unsymmetric 1,3-disubstituted urea.

As a process for preparing the symmetric 1,3-disubstituted urea, there can be cited a process for preparing the symmetric 1,3-disubstituted urea, comprising reacting the cyclic carbonic acid ester represented by the above formula (I) with an amine represented by the formula (II):

(II)

wherein $R^5$ is a linear or branched, alkyl group having 1 to 20 carbon atoms, alkenyl group having 2 to 20 carbon atoms or alkynyl group having 2 to 20 carbon atoms, which may have phenoxy group or an alkoxy group having 1 to 13 carbon atoms, a monocycloalkyl group having 3 to 8 carbon atoms, a bicycloalkyl group having 6 to 12 carbon atoms, an aryl group having 6 to 13 carbon atoms, furyl group, pyridyl group, or an aralkyl group having 7 to 20 carbon atoms, in the presence of an alkali metal alkoxide having 1 to 12 carbon atoms or a trialkylamine having 3 to 12 carbon atoms as a base (hereinafter referred to as Process I).

According to the Process I, there can be obtained a symmetric 1,3-disubstituted urea represented by the formula (III):

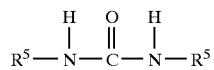
(III)

wherein $R^5$ is the same as defined above.

As a process for preparing the unsymmetric 1,3-disubstituted urea, there can be cited a process for preparing the unsymmetric 1,3-disubstituted urea, comprising reacting the cyclic carbonic acid ester with the amine represented by the formula (II) in the absence of a base at a temperature of 0° to 180° C., and thereafter with an amine represented by the formula (IV):

(IV)

wherein $R^6$ is different from $R^5$, and is a linear or branched, alkyl group having 1 to 20 carbon atoms, alkenyl group having 2 to 20 carbon atoms or alkynyl group having 2 to 20 carbon atoms, which may have phenoxy group or an alkoxy group having 1 to 13 carbon atoms, a monocycloalkyl group having 3 to 8 carbon atoms, a bicycloalkyl group having 6 to 12 carbon atoms, an aryl group having 6 to 13 carbon atoms, furyl group, pyridyl group, or an aralkyl group having 7 to 20 carbon atoms, in the presence of an alkali metal alkoxide having 1 to 12 carbon atoms or a trialkylamine having 3 to 12 carbon atoms (hereinafter referred to as Process II).

According to the Process II, there can be obtained an unsymmetric 1,3-disubstituted urea represented by the formula (V):

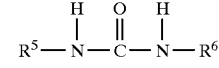
(V)

wherein $R^5$ and $R^6$ are the same as defined above.

First, the Process I is explained below.

The cyclic carbonic acid ester used in the Process I is represented by the formula (I) as explained above.

In the formula (I), each of $R^1$, $R^2$, $R^3$ and $R^4$ is independently hydrogen atom or a linear or branched alkyl group having 1 to 5 carbon atoms, and $R^1$ or $R^2$ may form a ring together with $R^3$ or $R^4$.

Examples of the alkyl group are, for instance, methyl group, ethyl group, propyl group, butyl group, pentyl group, and the like. Among them, hydrogen atom and methyl group are preferred.

It is desired that the ring which is formed by bonding $R^1$ or $R^2$ with $R^3$ or $R^4$ is a cycloalkyl group having 5 to 8 carbon atoms.

Examples of the cyclic carbonic acid ester represented by the formula (I) are, for instance, ethylene carbonate, propylene carbonate, 1,2-butylene carbonate, 2,3-butylene carbonate, 1,2-pentylene carbonate, 2,3-pentylene carbonate, 3-methyl-1,2-butylene carbonate, 2-methylpropylene carbonate, 2-methyl-2,3-butylene carbonate, 1,2-hexylene carbonate, 2,3-hexylene carbonate, 3,4-hexylene carbonate, 3-ethyl-3,4-butylene carbonate, 2-methyl-1,2-pentylene carbonate, cyclohexylene carbonate, cyclopentylene carbonate, cyclooctylene carbonate, and the like.

The amine used in the Process I is represented by the formula (II):

$$R^5-NH_2 \quad (II)$$

wherein $R^5$ is a linear or branched, alkyl group having 1 to 20 carbon atoms, alkenyl group having 2 to 20 carbon atoms or alkynyl group having 2 to 20 carbon atoms, which may have phenoxy group or an alkoxy group having 1 to 13 carbon atoms, a monocycloalkyl group having 3 to 8 carbon atoms, a bicycloalkyl group having 6 to 12 carbon atoms, an aryl group having 6 to 13 carbon atoms, furyl group, pyridyl group, or aralkyl group having 7 to 20 carbon atoms as explained above.

Examples of the linear or branched alkyl group having 1 to 20 carbon atoms, which may have phenoxy group or an alkoxy group having 1 to 13 carbon atoms are, for instance, linear or branched unsubstituted alkyl groups having 1 to 13 carbon atoms such as methyl group, ethyl group, propyl group, isopropyl group, butyl group, isobutyl group, sec-butyl group, tert-butyl group, pentyl group, and hexyl group; linear or branched substituted alkyl groups having 1 to 20 carbon atoms such as methoxymethyl group, ethoxymethyl group, tert-butoxymethyl group, methoxyethyl group, ethoxyethyl group and tert-butoxyethyl group; and the like. Among those alkyl groups, linear or branched alkyl groups having 1 to 8 carbon atoms are preferred in the present invention.

Examples of the linear or branched alkenyl group having 2 to 20 carbon atoms, which may have phenoxy group or an alkoxy group having 1 to 13 carbon atoms are, for instance, linear or branched unsubstituted alkenyl groups having 1 to 13 carbon atoms such as ethenyl group, 1-propenyl group, 2-propenyl group, 1-butenyl group, 2-butenyl group, and 1,3-butadienyl group. Among those alkenyl groups, linear or branched alkenyl groups having 2 to 8 carbon atoms are preferred in the present invention.

Examples of the linear or branched alkynyl group having 2 to 20 carbon atoms, which may have phenoxy group or an alkoxy group having 1 to 13 carbon atoms are, for instance, linear or branched unsubstituted alkynyl groups having 1 to 13 carbon atoms such as ethynyl group, 1-propynyl group, 2-propynyl group, 1-butynyl group, and 2-butynyl group. Among those alkynyl groups, linear or branched alkynyl groups having 2 to 8 carbon atoms are preferred in the present invention.

Examples of the monocycloalkyl group having 3 to 8 carbon atoms are, for instance, cyclopropyl group, cyclobutyl group, cyclopentyl group, cyclohexyl group, and the like.

Examples of the bicycloalkyl group having 6 to 12 carbon atoms are, for instance, norbornyl group, adamantyl group, and the like.

Examples of the aryl group having 6 to 13 carbon atoms are, for instance, phenyl group, naphthyl group, and the like. The aryl group may have a substituent such as a lower alkoxyl group having 1 to 5 carbon atoms, a halogen atom, amino group, nitro group or hydroxyl group.

Examples of the aralkyl group having 7 to 20 carbon atoms are, for instance, benzyl group, phenylethyl group, phenylpropyl group, phenylbutyl group, phenylpentyl group, and the like. Among them, aralkyl groups having 7 to 12 carbon atoms are preferred in the present invention.

The aralkyl group may have a substituent such as a alkoxyl group having 1 to 4 carbon atoms, for example, methoxy group, ethoxy group, propoxy group, isopropoxy group, ethenylamine, 1-propenylamine, 2-propenylamine, 2-butenylamine, 1,3-butadienylamine, ethynylamine, 2-propynylamine, and the like.

Concrete examples of the amine represented by the formula (II) include methylamine, ethylamine, propylamine, isopropylamine, cyclopropylamine, n-butylamine, isobutylamine, sec-butylamine, tert-butylamine, cyclobutylamine, 1-pentylamine, 2-pentylamine, 3-pentylamine, 3-methyl-2-butylamine, neopentylamine, cyclopentylamine, 2-methyl-2-butylamine, 1-hexylamine, 2-hexylamine, 3-hexylamine, 3-methyl-2-pentylamine, 4-methyl-2-pentylamine, 2,2-dimethylbutylamine, 2-methyl-2-pentylamine, cyclohexylamine, 1-heptylamine, 2-heptylamine, 3-heptylamine, 4-heptylamine, 3-methyl-2-hexylamine, 4-methyl-2-hexylamine, 5-methyl-2-hexylamine, 2,2-dimethylpentylamine, 3,3-dimethyl-2-pentylamine, 2-methyl-2-heptylamine, cycloheptylamine, 1-octylamine, 2-octylamine, 3-octylamine, 4-octylamine, 3-methyl-2-octylamine, 4-methyl-2-octylamine, 5-methyl-2-octylamine, 2,2-dimethylhexylamine, cyclooctylamine, 3-methyl-2-heptylamine, 4-methyl-2-heptylamine, 5-methyl- 2-heptylamine, nonylamine, decylamine, undecylamine, dodecylamine, tridecylamine, tetradecylamine, pentadecylamine, hexadecylamine, heptadecylamine, octadecylamine, nonadecylamine, icosylamine, 1-methoxy-2-ethylamine, 1-methoxy-2-propylamine, 1-methoxy-3-propylamine, 1-methoxy-2-butylamine, 1-methoxy-3-butylamine, 1-methoxy-4-butylamine, 1-methoxy-5-pentylamine, 1-methoxy-6-hexylamine, 1-methoxy-7-heptylamine, 1-methoxy-8-octylamine, 1-methoxy-9-nonylamine, 1-methoxy-10-decylamine, 1-ethoxy-2-ethylamine, 1-ethoxy-3-propylamine, 1-ethoxy-4-butylamine, 1-ethoxy-5-pentylamine, 1-ethoxy-6-hexylamine, 1-ethoxy-7-heptylamine, 1-ethoxy-8-octylamine, 1-ethoxy-9-nonylamine, 1-ethoxy-10-decylamine, 1-propoxy-2-ethylamine, 1-butoxy-2-ethylamine, 1-pentyloxy-2-ethylamine, 1-hexyloxy-2-ethylamine, 1-heptyloxy-2-ethylamine, 1-octyloxy-2-ethylamine, 1-nonyloxy-2-ethylamine, 1-decyloxy-2-ethylamine, 1-undecyloxy-2-ethylamine, 1-dodecyloxy-2-ethylamine, 1-tridecyloxy-2-ethylamine, aniline, benzylamine, α-methylbenzylamine, 2-chloroaniline, 3-chloroaniline, 4-chloroaniline, 2-aminopyridine, 2-phenylethylamine, 3-phenyl-1-propylamine, 3-phenyl-2-propylamine, 3-phenyl-3-propylamine, 4-phenyl-2-butylamine, 1-isopropoxy-2-ethylamine, 1-isopropoxy-2-propylamine, 1-isopropoxy-3-propylamine, 1-isopropoxy-3-butylamine, 1-phenoxy-2-ethylamine, 1-phenoxy-2-propylamine, 1-phenoxy-3-propylamine, 1-phenoxy-4-butylamine, 2-norbornylamine, and the like.

The amount of the amine represented by the formula (II) is theoretically 2 moles per one mole of the cyclic carbonic acid ester. Accordingly, as to the Process I, it is desired that the amount of the amine is at least 2 moles, preferably at least 2.5 moles, more preferably at least 3 moles per one mole of the cyclic carbonic acid ester. Also, from the viewpoint of economics, it is desired that the amount of the amine is at most 20 moles, preferably at most 10 moles, more preferably at most 5 moles per one mole of the cyclic carbonic acid ester.

In the present invention, since there is no necessity to use the amine represented by the formula (II) in a large excess amount, there is no necessity to recover the unreacted amine after the reaction is completed. Also, even though the amine is used in a large excess amount, there is no problem in the reaction.

According to the Process I, the cyclic carbonic acid ester is reacted with the amine represented by the formula (II) in the presence of an alkali metal alkoxide having 1 to 12 carbon atoms or a trialkylamine having 3 to 12 carbon atoms as a base.

The Process I has a great characteristic in that an alkali metal alkoxide having 1 to 6 carbon atoms or a trialkylamine having 3 to 12 carbon atoms is used as a base. When the alkali metal alkoxide having 1 to 6 carbon atoms or the trialkylamine having 3 to 12 carbon atoms is used as a base, a symmetric 1,3-disubstituted urea can be obtained in a high yield by its catalytic action without high temperature and high pressure conditions even though the alkali metal alkoxide or the trialkylamine is used in a small amount.

Examples of the alkali metal alkoxide having 1 to 12 carbon atoms are, for instance, sodium methoxide, sodium ethoxide, potassium tert-butoxide, titanium isopropoxide, and the like.

Examples of the trialkylamine having 3 to 12 carbon atoms are, for instance, trimethylamine, triethylamine, tripropylamine, tributylamine, and the like.

The alkali metal alkoxide having 1 to 12 carbon atoms and the trialkylamine having 3 to 12 carbon atoms can be used as a solution by dissolving in a solvent such as methanol as occasion demands.

It is desired that the amount of the alkali metal alkoxide having 1 to 12 carbon atoms and the trialkylamine having 3 to 12 carbon atoms is at least 0.1 mmole, preferably at least 10 mmoles, more preferably at least 0.1 mole per one mole of the cyclic carbonic acid ester in order to progress the reaction higher. Also, it is desired that the amount is at most 5 moles, preferably at most 1 mole, more preferably at most 0.5 moles per one mole of the cyclic carbonic acid ester from the viewpoint of economics.

According to the Process I, the reaction can be carried out without a solvent, but the solvent can be used if necessary. Examples of the solvent are, for instance, hydrocarbons such as pentane, hexane, cyclohexane, heptane, pinane, nonane, o-cymene, m-cymene, p-cymene, benzine distillates having a boiling point of from 70 to 190° C., methylcyclohexane, decalin, petroleum ether, ligroin, 2,2,4-trimethylpentane, 2,2,3-trimethylpentane, 2,3,3-trimethylpentane, octane, benzene, toluene, xylene, naphthalene and tetralin; ethers such as diethyl ether, ethyl propyl ether, methyl tert-butyl ether, dibutyl ether, diisobutyl ether, diisopentyl ether, diisopropyl ether, anisole, phenetole, cyclohexyl methyl ether, ethyleneglycol dimethyl ether, tetrahydrofuran, dioxane, thioanisole; nitriles such acetonitrile and propionitrile; alcohols such as methanol, ethanol, 1-propanol, 2-propanol, 2-methyl-2-propanol and 1-butanol, and the like. Those solvents can be used alone or in an admixture thereof. Among them, toluene and cyclohexane are preferred.

It is desired that the amount of the solvent is adjusted so that the amount of the cyclic carbonic acid ester represented by the formula (I) is 1 to 200 parts by weight or so based upon 100 parts by weight of the solvent.

It is desired that the reaction temperature is at least 50° C., preferably at least 90° C. in order to make progress in the reaction. Also, it is desired that the reaction temperature is at most 180° C., preferably at most 140° C. from the viewpoint of workability and economics.

The reaction time cannot be absolutely determined because the reaction time varies depending upon reaction temperature and the like. The reaction time can be usually 1 to 5 hours or so.

The pressure during the reaction is not particularly limited in the Process I because the reaction proceeds rapidly at the above reaction temperature. The pressure can be usually within 0 to 3 kgf/cm² or so.

The atmosphere during the reaction is not particularly limited. The atmosphere can be, for instance, air or inert gas such as nitrogen gas.

After the reaction is completed, a symmetric 1,3-disubstituted urea represented by the formula (III):

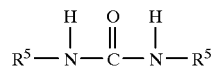

(III)

wherein $R^5$ is the same as defined above, can be usually obtained as crystals.

When a poor solvent to the symmetric 1,3-disubstituted urea is used, crystals of the symmetric 1,3-disubstituted urea are contained in the resulting reaction product after the reaction is completed. The crystals of the 1,3-disubstituted urea can be furthermore obtained when the reaction product is cooled to a temperature of 10° to 30° C. or so.

When a solvent is not used or when a good solvent to the symmetric 1,3-disubstituted urea is used, in order to increase the yield of the symmetric 1,3-disubstituted urea, it is desired that the resulting reaction solution is cooled to a temperature of 10° to 30° C. or so, that a poor solvent to the symmetric 1,3-disubstituted urea is added to the reaction solution, and that the solution is stirred for about 0.5 to about 2 hours.

As the poor solvent, there can be cited, for instance, water, acetone, methanol, ethanol, isopropanol, and the like.

Then, the resulting crystals of the symmetric 1,3-disubstituted urea can be isolated from the reaction solution by filtering the reaction solution, and washing and drying the crystals in a conventional method.

In the Process I, the crystals of the symmetric 1,3-disubstituted urea can be purified by recrystallizing if necessary.

The symmetric 1,3-disubstituted urea obtained in the Process I is useful as an intermediate for the preparation of pharmaceuticals and agricultural chemicals. In particular, the symmetric 1,3-disubstituted urea is useful as an intermediate for the preparation of an alkylxanthine as disclosed in Japanese Unexamined Patent Publication No. 4-221384 and International Publication No. WO 95/23148, and an intermediate for the preparation of a phenylxanthine compound as disclosed in Japanese Unexamined Patent Publication No. 58-189181.

Second, the Process II is explained below.

According to the Process II, an unsymmetric 1,3-disubstituted urea represented by the formula (V):

(V)

wherein $R^5$ is the same as defined above, and $R^6$ is different from $R^5$ and is a linear or branched, alkyl group having 1 to 20 carbon atoms, alkenyl group having 2 to 20 carbon atoms or alkynyl group having 2 to 20 carbon atoms, which may have phenoxy group or an alkoxy group having 1 to 13 carbon atoms, a monocycloalkyl group having 3 to 8 carbon atoms, a bicycloalkyl group having 6 to 12 carbon atoms, an aryl group having 6 to 13 carbon atoms, furyl group, pyridyl group, or an aralkyl group having 7 to 20 carbon atoms, can be obtained by reacting the cyclic carbonic acid ester represented by the above formula (I) with the amine represented by the formula (II) in the absence of a base at a temperature of 0° to 180° C., and thereafter with an amine represented by the formula (IV):

$$R^6-NH_2 \quad (IV)$$

wherein $R^6$ is the same as defined above, in the presence of an alkali metal alkoxide having 1 to 12 carbon atoms or a trialkylamine having 3 to 12 carbon atoms as a base.

The cyclic carbonic acid ester represented by the formula (I) which is used in the Process II can be the same as that used in the Process I. As the amine which is reacted with the cyclic carbonic acid ester, there can be used the same amine represented by the formula (II) as used in the Process I.

The amount of the amine represented by the formula (II) is theoretically one mole per one mole of the cyclic carbonic acid ester. Accordingly, it is desired in the Process II that the amount of the amine is at least one mole per one mole of the cyclic carbonic acid ester. When the amine represented by the formula (II) is used in a large excess amount, there is a necessity to remove the excessive amine after the reaction. Therefore, it is desired that the amount of the amine is at most 10 moles, preferably at most 3 moles, more preferably at most 1.5 moles per one mole of the cyclic carbonic acid ester.

According to the Process II, an unsymmetric 1,3-disubstituted urea represented by the formula (V) is obtained because the cyclic carbonic acid ester represented by formula (I) is reacted with the amine represented by the formula (II) in the absence of a base which is different from the Process I at the first stage reaction, and thereafter with the amine represented by the formula (IV) in the presence of the above base, that is, an alkali metal alkoxide having 1 to 12 carbon atoms or an trialkylamine having 3 to 12 carbon atoms at the second stage reaction.

The temperature during the reaction of the cyclic carbonic acid ester with the amine represented by the formula (II) is at least 0° C., preferably at least 50° C. to smoothly proceed the reaction, and at most 180° C., preferably at most 140° C. to add only one molecule of the amine to one molecule of the cyclic carbonic acid ester.

The reaction time cannot be absolutely determined because the reaction time varies depending upon the reaction temperature. The reaction time is usually 0.5 to 3 hours or so.

The atmosphere during the reaction is not particularly limited. The atmosphere can be, for instance, air or inert gas such as nitrogen gas.

The reaction can be carried out without a solvent. The solvent may be used as occasion demands. As the above solvent, there can be exemplified, for instance, the solvents used in the Process I.

It is desired that the amount of the solvent is adjusted so that the amount of the cyclic carbonic acid ester is 1 to 200 parts by weight or so based upon 100 parts by weight of the solvent.

After the reaction of the cyclic carbonic acid ester with the amine represented by the formula (II), the resulting reaction product can be used as it is. Alternatively, the reaction product can be used after the unreacted amine remaining in the reaction product is removed from the reaction product by means of distillation. The resulting reaction product is then reacted with the amine represented by the formula (IV) in the presence of an alkali metal alkoxide having 1 to 12 carbon atoms or a trialkylamine having 3 to 12 carbon atoms as a base.

As the alkali metal alkoxide having 1 to 12 carbon atoms used in the Process II, there can be cited, for instance, the same alkali metal alkoxide having 1 to 12 carbon atoms as used in the Process I.

As the trialkylamine having 3 to 12 carbon atoms used in the Process II, there can be used the same trialkylamine having 3 to 12 carbon atoms as used in the Process I.

The alkali metal alkoxide having 1 to 12 carbon atoms and the trialkylamine having 3 to 12 carbon atoms can be used as a solution by dissolving in a solvent such as methanol as occasion demands.

The amount of the alkali metal alkoxide having 1 to 12 carbon atoms and the trialkylamine having 3 to 12 carbon atoms can be the same as in the Process I.

As the amine represented by the formula (IV) used in the Process II, there can be cited the amine represented by the formula (II). However, the group $R^6$ is different from the group $R^5$ shown in the formula (II) in order to give an unsymmetric 1,3-disubstituted amine in the Process II.

It is desired that the amount of the amine represented by the formula (IV) is at least one mole per one mole of the cyclic carbonic acid ester because one mole of the amine is theoretically necessitated per one mole of the cyclic carbonic acid ester. Also, it is desired that the amount of the amine is at most 10 moles, preferably at most 3 moles, more preferably at most 1.5 moles per one mole of the cyclic carbonic acid ester from the viewpoint of economics.

During the reaction of the reaction product of the cyclic carbonic acid ester and the amine represented by the formula (II), with the amine represented by the formula (IV), it is desired that the reaction temperature is at least 50° C., preferably at least 90° C. in order to smoothly progress the reaction. Also, it is desired that the reaction temperature is at most 180° C., preferably at most 140° C. in order to inhibit the generation of by-products.

The reaction time cannot be absolutely determined because the reaction time varies depending upon the reaction temperature and the like. The reaction time is usually 0.5 to 3 hours or so.

Also, the atmosphere during the reaction is not particularly limited. The atmosphere can be air or inert gas such as nitrogen gas.

The reaction can be carried out without a solvent. However, a solvent can be used as occasion demands. As the solvent, there can be cited, for instance, the solvents which can be used during the reaction of the cyclic carbonic acid ester represented by the formula (I) with the amine represented by the formula (II).

It is desired that the amount of the solvent is adjusted so that the amount of the cyclic carbonic acid ester represented by the formula (I) is 1 to 200 parts by weight or so on the basis of 100 parts by weight of the solvent.

After the reaction is completed, an unsymmetric 1,3-disubstituted urea represented by the formula (V):

wherein $R^5$ and $R^6$ are the same as defined above, can be usually collected in the form of crystals.

When a poor solvent to the unsymmetric 1,3-disubstituted urea is used as the solvent, crystals of the unsymmetric 1,3-disubstituted urea are generated in the resulting reaction product during the reaction. The crystals of the unsymmetric 1,3-disubstituted urea can be furthermore obtained when the reaction product is cooled to a temperature of 10° to 30° C. or so.

When a solvent is not used or when a good solvent to the unsymmetric 1,3-disubstituted urea is used, in order to increase the yield of the unsymmetric 1,3-disubstituted urea, it is desired that the resulting reaction solution is cooled to a temperature of 10° to 30° C. or so, a poor solvent to the unsymmetric 1,3-disubstituted urea is added to the reaction solution, and the reaction solution is stirred for about 0.5 to about 2 hours.

As the poor solvent, there can be cited, for instance, water, acetone, methanol, ethanol, isopropanol, and the like.

Then, the resulting crystals of the unsymmetric 1,3-disubstituted urea can be isolated from the reaction solution by filtering the reaction solution, and washing and drying the crystals in a conventional method.

In the Process II, the crystals of the unsymmetric 1,3-disubstituted urea can be purified by recrystallizing if necessary.

The unsymmetric 1,3-disubstituted urea obtained in the Process II is useful as an intermediate for the preparation of pharmaceuticals and agricultural chemicals. In particular, the unsymmetric 1,3-disubstituted urea is useful as an intermediate for the preparation of phenylxanthine as disclosed in Japanese Unexamined Patent Publication No. 58-189181.

According to the Process I and Process II, since toxic phosgene and isocyanate, which have been used as starting materials in conventional methods, are not necessitated, a 1,3-disubstituted urea can be safely prepared with excellent workability.

Also, since the alkali metal alkoxide having 1 to 12 carbon atoms and the trialkylamine having 3 to 12 carbon atoms, which are used as bases, exhibit excellent catalytic action, a 1,3-disubstituted urea can be obtained in a high yield without severe reaction conditions such as high temperatures and high pressures. Therefore, the Process I and the Process II do not necessitate a large and complex apparatus for preparing the 1,3-disubstituted urea, and the 1,3-disubstituted urea can be safely prepared with good workability.

Moreover, since the Process I and the Process II do not necessitate expensive bis(4-nitrophenyl)carbonate as a starting material, the 1,3-disubstituted urea can be obtained in low costs.

Accordingly, the Process I and the Process II are excellent in workability, safety and economics.

EXAMPLES

The present invention is hereinafter described in more detail by means of the following working examples, which are not to be construed as limitative.

Example 1

A 150 ml autoclave was charged with 31.0 g (0.525 moles) of propylamine and 15.4 g (0.175 moles) of ethylene carbonate. Thereafter, 3.38 g of a 28% methanol solution of sodium methoxide (0.0175 moles) was added to the autoclave, and the resulting mixture was heated to a temperature of 95° to 100° C. for 3 hours with stirring. At that time, the internal pressure of the autoclave attained to 3 kgf/cm$^2$.

After the reaction was completed, the resulting reaction solution was cooled to 25° C., and 150 ml of water was added to the reaction solution. Then, the mixture was stirred for one hour. After the resulting crystals were filtered off and washed twice with 25 ml of water, the resulting white crystals were dried under reduced pressure to give 21.5 g (0.149 moles) of 1,3-dipropyl urea in a 85.1% yield.

The resulting crystal was identified as 1,3-dipropyl urea by the following physical properties. Melting point: 105° C. (lit. 105° C.) $^1$H-NMR (270 MHz, CDCl$_3$) δ (ppm): 0.91 (t, 6H), 1.50 (dt, 4H), 3.11 (t, 4H), 5.11–5.23 (br, 2H)

Example 2

A 150 ml autoclave was charged with 27.8 g (0.470 moles) of propylamine and 16.0 g (0.157 moles) of propylene carbonate. Thereafter, 3.03 g of a 28% methanol solution of sodium methoxide (0.0157 moles) was added to the autoclave, and the resulting mixture was heated to a temperature of 95° to 105° C. for 3 hours with stirring. At that time, the internal pressure of the autoclave attained to 3 kgf/cm$^2$.

After the reaction was completed, the resulting reaction solution was cooled to 25° C., and 150 ml of water was added to the reaction solution. Then, the mixture was stirred for one hour. After the resulting crystals were filtered off and washed twice with 25 ml of water, the resulting white crystals were dried under reduced pressure to give 18.2 g (0.126 moles) of 1,3-dipropyl urea in a 80.3% yield.

The resulting crystal was identified as 1,3-dipropyl urea in the same manner as in Example 1.

Example 3

A 150 ml autoclave was charged with 31.0 g (0.525 moles) of propylamine and 15.4 g (0.175 moles) of ethylene carbonate. Thereafter, 1.8 g (0.0175 moles) of triethylamine was added to the autoclave, and the resulting mixture was heated to a temperature of 95° to 100° C. for 3 hours with stirring. At that time, the internal pressure of the autoclave attained to 3 kgf/cm$^2$.

After the reaction was completed, the resulting reaction solution was cooled to 25° C., and 150 ml of water was added to the reaction solution. Then, the mixture was stirred for one hour. After the resulting crystals were filtered off and washed twice with 25 ml of water, the resulting white crystals were dried under reduced pressure to give 14.5 g (0.101 moles) of 1,3-dipropyl urea in a 57.1% yield.

The resulting crystal was identified as 1,3-dipropyl urea in the same manner as in Example 1.

Example 4

A 300 ml four-necked flask was charged with 57.0 g (0.613 moles) of aniline and 15.4 g (0.175 moles) of ethylene carbonate. Thereafter, 3.38 g of a 28% methanol solution of sodium methoxide (0.0175 moles) was added to the flask, and the resulting mixture was heated to a temperature of 95° to 100° C. for 3 hours with stirring.

After the reaction was completed, the resulting reaction solution was cooled to 25° C., and 150 ml of acetone was added to the reaction solution. Then, the mixture was stirred for one hour. After the resulting crystals were filtered off and washed twice with 25 ml of water, the resulting white crystals were dried under reduced pressure to give 24.1 g (0.114 moles) of 1,3-diphenyl urea in a 65.0% yield.

The resulting crystal was identified as 1,3-diphenyl urea by the following physical properties. Melting point: 238° C. (lit. 238° C.) $^1$H-NMR (270 MHz, CDCl$_3$+DMSO-d$_6$) δ (ppm): 6.90–6.98 (m, 2H), 7.15–7.27 (m, 4H), 7.43–7.48 (m, 4H), 8.41–8.52 (br, 2H)

Example 5

A 200 ml four-necked flask was charged with 6.75 g (68.1 mmoles) of cyclohexylamine and 2.00 g (22.7 mmoles) of ethylene carbonate. Thereafter, 0.44 g of a 28% methanol solution of sodium methoxide (2.3 mmoles) was added to the flask, and the resulting mixture was heated to a temperature of 95° to 100° C. for 3 hours with stirring.

After the reaction was completed, the resulting reaction solution was cooled to 25° C., and 50 ml of methanol was added to the reaction solution. Then, the mixture was stirred for one hour. After the resulting crystals were filtered off and washed twice with 25 ml of water, the resulting white crystals were dried under reduced pressure to give 2.76 g (12.3 mmoles) of 1,3-dicyclohexyl urea in a 54.2% yield.

The resulting crystal was identified as 1,3-dicyclohexyl urea by the following physical properties. Melting point: 232° C. (lit. 232°–233° C.) $^1$H-NMR (270 MHz, CDCl$_3$) δ (ppm): 1.18–1.50 (m, 10H), 1.66–2.11 (m, 10H), 3.54–3.69 (m, 2H)

Example 6

A 150 ml autoclave was charged with 46.6 g (0.816 moles) of allylamine and 3.57 g of a 28% methanol solution of sodium methoxide (0.019 moles). Thereafter, 32.7 g (0.371 moles) of ethylene carbonate was added to the autoclave little by little with stirring. After the addition of ethylene carbonate, the mixture was heated to 100° to 115° C. and stirred for 3 hours at the temperature. At that time, the internal pressure of the autoclave attained to 1.5 kgf/cm$^2$.

After the reaction was completed, the resulting reaction solution was cooled to 25° C., and added to 160 ml of water which was previously added to a 300 ml four-necked flask. Then, the resulting mixture was stirred at 10° C. for one hour.

After the resulting crystals were filtered off and washed twice with 25 ml of water, the resulting white crystals were dried under reduced pressure to give 37.0 g (0.264 moles) of 1,3-di-(2-propenyl) urea in a 71.2% yield.

Example 7

A 300 ml four-necked flask was charged with 4.02 g (0.0681 moles) of propylamine and 6.00 g (0.0681 moles) of ethylene carbonate, and the resulting mixture was refluxed at about 50° C. for one hour. Then, 6.75 g (0.0681 moles) of cyclohexylamine and 1.3 g of a 28% methanol solution of sodium methoxide (0.0067 moles) were added to the flask, and the mixture was heated at 110° C. for 2 hours with stirring. At that time, the conversion of ethylene carbonate was 93% when measured by high performance liquid chromatography.

After the reaction was completed, the resulting reaction solution was cooled to 25° C., 100 ml of acetone was added thereto and stirred for 30 minutes. Then, 100 ml of water was added to the reaction solution to crystallize and stirred for one hour.

After the resulting crystals were filtered off and washed twice with 25 ml of water. The resulting white crystals were dried under reduced pressure to give 11.7 g (0.0635 moles) of 1-cyclohexyl-3-propyl urea in a 93.1% yield.

The resulting crystal was identified as 1-cyclohexyl-3-propyl urea by the following physical properties. Melting point: 108–109° C. (lit. 106–107° C.) $^1$H-NMR (270 MHz, DMSO-d$_6$) δ (ppm): 0.90 (t, 3H), 1.43 (m, 2H), 1.06–1.83 (m, 10H), 3.00 (dd, 2H), 3.36–3.47 (m, 1H), 5.72–5.79 (m, 2H)

Example 8

A 300 ml four-necked flask was charged with 10.3 g (0.175 moles) of propylamine and 15.4 g (0.175 moles) of ethylene carbonate, and the mixture was refluxed at about 50° C. for one hour. Then, 16.3 g (0.175 moles) of aniline and 1.3 g of a 28% methanol solution of sodium methoxide (0.067 moles) were added to the flask, and the resulting mixture was heated at 110° C. for 3 hours with stirring. At that time, the conversion of ethylene carbonate was 90% when measured by high performance liquid chromatography.

After the reaction was completed, the resulting reaction solution was cooled to 25° C., 100 ml of water was added to the reaction solution. Then, 15 g of concentrated hydrochloric acid was added dropwise to the reaction solution to crystallize, and the mixture was stirred for one hour.

After the resulting crystals were filtered off and washed twice with 25 ml of water. The resulting white crystals were dried under reduced pressure to give 17.7 g (0.0993 moles) of 1-phenyl-3-propyl urea in a 56.7% yield.

The resulting crystal was identified as 1-phenyl-3-propyl urea by the following physical properties. Melting point: 106°–107° C. (lit. 114° C.) $^1$H-NMR (270 MHz, DMSO-d$_6$) δ (ppm): 0.90 (t, 3H), 1.43–1.50 (m, 2H), 3.00–3.11 (m, 2H), 6.90–6.98 (m, 1H), 7.15–7.27 (m, 2H), 7.43–7.48 (m, 2H)

Example 9

A 300 ml four-necked flask was charged with 4.02 g (0.0681 moles) of propylamine and 6.00 g (0.0681 moles) of ethylene carbonate, and the mixture was refluxed at about 50° C. for one hour. Then, 6.75 g (0.0681 moles) of cyclohexylamine and 0.63 g (0.0061 moles) of triethylamine were added to the flask, and the resulting mixture was heated at 110° C. for 2 hours with stirring. At that time, the conversion of ethylene carbonate was 90% when measured by high performance liquid chromatography.

After the reaction was completed, the reaction solution was cooled to 25° C., and 100 ml of acetone was added to the reaction solution, and the mixture was stirred for 30 minutes. Then, 100 g of water was added to the mixture to crystallize, and the mixture was stirred for one hour. After the resulting crystals were filtered off and washed twice with 25 ml of water, the resulting white crystals were dried under reduced pressure to give 7.23 g (0.0392 moles) of 1-cyclohexyl-3-propyl urea in a 57.4% yield.

The resulting crystal was identified as 1-cyclohexyl-3-propyl urea in the same manner as in Example 7.

Comparative Example 1

The same procedures as in Example 1 were carried out except that the methanol solution of sodium methoxide was not used.

As a result, the yield of 1,3-dipropyl urea was 1.0%.

Comparative Example 2

To 31.0 g (0.525 moles) of propylamine which was previously charged in a 150 ml autoclave, 15.4 g (0.175 moles) of ethylene carbonate was added, and the mixture was heated with stirring at 111° C. for 3 hours. At that time, the internal pressure of the autoclave attained to 5 kgf/cm$^2$.

After the reaction was completed, the resulting reaction solution was cooled to 25° C., 150 ml of water was added to the reaction solution, and then the mixture was stirred for one hour. After the resulting crystals were filtered off and washed twice with 25 ml of water, the resulting white crystals were dried under reduced pressure to give 5.26 g (0.0365 moles) of 1,3-dipropyl urea in a 20.8% yield.

The resulting crystal was identified as 1,3-dipropyl urea in the same manner as in Example 1.

From the results of Examples 1 to 9, according to the process for preparing a 1,3-disubstituted urea of the present invention, it can be seen that the 1,3-disubstituted urea can be obtained in good workability and high yield because the process does not necessitate severe reaction conditions such as high temperatures and high pressures which require a large and complex apparatus for preparing the 1,3-disubstituted urea. Moreover, according to the process of the present invention, the 1,3-disubstituted urea can be safely obtained because the process does not necessitate toxic phosgene and isocyanate. Furthermore, according to the process of the present invention, the 1,3-disubstituted urea can be obtained in good economics because the process does not necessitate expensive bis(4-nitrophenyl)carbonate.

As stated above, according to the present invention, the 1,3-disubstituted urea can be obtained in good workability, safety, yield and economics.

The present invention being thus described, it will be obvious that the same may be varied in many ways. Such variations are not to be regarded as a departure from the spirit and scope of the present invention, all such modification as would be obvious to one skilled in the art are intended to be included within the scope of the following claims.

What is claimed is:

1. A process for preparing a symmetric 1,3-disubstituted urea represented by the formula (III):

(III)

wherein $R^5$ is a linear or branched, alkyl group having 1 to 20 carbon atoms, alkenyl group having 2 to 20 carbon atoms or alkynyl group having 2 to 20 carbon atoms, which may have phenoxy group or an alkoxy group having 1 to 13 carbon atoms, a monocycloalkyl group having 3 to 8 carbon atoms, a bicycloalkyl group having 6 to 12 carbon atoms, an aryl group having 6 to 13 carbon atoms, furyl group, pyridyl group, or an aralkyl group having 7 to 20 carbon atoms, comprising reacting a cyclic carbonic acid ester represented by the formula (I):

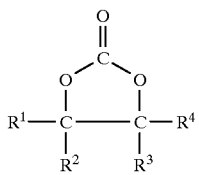
(I)

wherein each of $R^1$, $R^2$, $R^3$ and $R^4$ is independently hydrogen atom or a linear or branched alkyl group having 1 to 5 carbon atoms, and $R^1$ or $R^2$ may form a ring together with $R^3$ or $R^4$, with an amine represented by the formula (II):

$$R^5\text{—}NH_2 \qquad (II)$$

wherein $R^5$ is the same as defined above, in the presence of an alkali metal alkoxide having 1 to 12 carbon atoms or a trialkylamine having 3 to 12 carbon atoms as a base.

2. The process for preparing a symmetric 1,3-disubstituted urea of claim 1, wherein the amount of the amine represented by the formula (II) is 2 to 20 moles per one mole of the cyclic carbonic acid ester.

3. A process for preparing an unsymmetric 1,3-disubstituted urea represented by the formula (V):

(V)

wherein $R^5$ is different from $R^6$, and each of $R^5$ and $R^6$ is independently a linear or branched, alkyl group having 1 to 20 carbon atoms, alkenyl group having 2 to 20 carbon atoms or alkynyl group having 2 to 20 carbon atoms, which may have phenoxy group or an alkoxy group having 1 to 13 carbon atoms, a monocycloalkyl group having 3 to 8 carbon atoms, a bicycloalkyl group having 6 to 12 carbon atoms, an aryl group having 6 to 13 carbon atoms, furyl group, pyridyl group, or an aralkyl group having 7 to 20 carbon atoms, comprising reacting a cyclic carbonic acid ester represented by the formula (I):

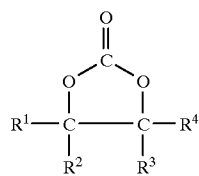
(I)

wherein each of $R^1$, $R^2$, $R^3$ and $R^4$ is independently hydrogen atom or a linear or branched alkyl group having 1 to 5 carbon atoms, and $R^1$ or $R^2$ may form a ring together with $R^3$ or $R^4$, with an amine represented by the formula (II):

(II)

wherein $R^5$ is the same as defined above, in the absence of a base at a temperature of 0° to 180° C., and thereafter with an amine represented by the formula (IV):

(IV)

wherein $R^6$ is the same as defined above, in the presence of an alkali metal alkoxide having 1 to 12 carbon atoms or a trialkylamine having 3 to 12 carbon atoms as a base.

* * * * *